(12) United States Patent
Walther et al.

(10) Patent No.: US 10,952,840 B2
(45) Date of Patent: Mar. 23, 2021

(54) VASCULAR PROSTHESIS WITH SIDE BRANCHES

(71) Applicant: JOTEC GmbH, Hechingen (DE)

(72) Inventors: Michael Walther, Lentfoehrden (DE); Karsten Klein, Moessingen (DE); Juergen Merz, Balingen (DE); Jan Ulmer, Sindelfingen (DE)

(73) Assignee: JOTEC GMBH, Hechingen (DE)

( * ) Notice: Subject to any disclaimer, the term of this patent is extended or adjusted under 35 U.S.C. 154(b) by 108 days.

(21) Appl. No.: 16/051,895

(22) Filed: Aug. 1, 2018

(65) Prior Publication Data

US 2019/0029798 A1    Jan. 31, 2019

Related U.S. Application Data

(63) Continuation of application No. PCT/EP2017/052336, filed on Feb. 3, 2017.

(30) Foreign Application Priority Data

Feb. 4, 2016 (DE) ............... 10 2016 102 008.7

(51) Int. Cl.
*A61F 2/07* (2013.01)
*A61F 2/90* (2013.01)
(Continued)

(52) U.S. Cl.
CPC ............ *A61F 2/07* (2013.01); *A61F 2/90* (2013.01); *A61F 2/89* (2013.01);
(Continued)

(58) Field of Classification Search
CPC ............ A61F 2/07–2/075; A61F 2/89; A61F 2002/823; A61F 2002/061;
(Continued)

(56) References Cited

U.S. PATENT DOCUMENTS

2004/0111148 A1* 6/2004 Goodson ............... A61F 2/07
                                                            623/1.16
2005/0102018 A1  5/2005 Carpenter et al.
(Continued)

FOREIGN PATENT DOCUMENTS

EP  2606851 A1  6/2013
EP  2740441 A1  6/2014
(Continued)

OTHER PUBLICATIONS

European Patent Office, Written opinion for PCT/EP2017/052336, dated Aug. 7, 2018, 7 pages (with extra 7 pages of English translation).
(Continued)

*Primary Examiner* — Paul B Prebilic
(74) *Attorney, Agent, or Firm* — Rimon P.C.

(57) ABSTRACT

The present invention relates a vascular prosthesis for a blood vessel of a patient, which has the following: a hollow-cylindrical main body with a main lumen extending therein, an also a multiplicity of stent rings, which are not connected to one another, are arranged spaced apart one behind the other in the longitudinal direction of the vascular prosthesis and running around in a meandering formation. The vascular prosthesis also has four side branches, which extend distally into the main lumen from fenestrations in the prosthesis material lying between the stent rings.

16 Claims, 3 Drawing Sheets

(51) Int. Cl.
*A61F 2/89* (2013.01)
*A61F 2/06* (2013.01)
*A61F 2/82* (2013.01)

(52) U.S. Cl.
CPC ... *A61F 2002/061* (2013.01); *A61F 2002/823* (2013.01); *A61F 2250/0039* (2013.01)

(58) Field of Classification Search
CPC ...... A61F 2220/0075; A61F 2230/0008; A61F 2250/0039; A61F 2250/006–2250/0063
See application file for complete search history.

(56) References Cited

U.S. PATENT DOCUMENTS

| | | | | |
|---|---|---|---|---|
| 2006/0184228 | A1* | 8/2006 | Khoury | A61F 2/07 623/1.13 |
| 2006/0195177 | A1 | 8/2006 | Kaufmann et al. | |
| 2009/0319022 | A1* | 12/2009 | Hartley | A61F 2/07 623/1.13 |
| 2013/0046371 | A1* | 2/2013 | Greenberg | A61F 2/07 623/1.11 |
| 2013/0138199 | A1* | 5/2013 | Ivancev | A61F 2/82 623/1.11 |
| 2013/0274857 | A1* | 10/2013 | Quinn | A61F 2/07 623/1.11 |
| 2013/0345785 | A1 | 12/2013 | Hartley et al. | |
| 2014/0094902 | A1 | 4/2014 | Khoury | |
| 2014/0180394 | A1* | 6/2014 | Greenberg | A61F 2/07 623/1.15 |
| 2014/0336745 | A1 | 11/2014 | Barthold et al. | |
| 2015/0148890 | A1 | 5/2015 | Hartley et al. | |
| 2016/0081787 | A1* | 3/2016 | Parodi | A61F 2/07 623/1.14 |
| 2017/0007392 | A1 | 1/2017 | Lourenco et al. | |

FOREIGN PATENT DOCUMENTS

| | | |
|---|---|---|
| JE | 10337739 A1 | 3/2005 |
| JE | 102012101103 B3 | 7/2013 |
| WO | 2015/109375 A1 | 7/2015 |

OTHER PUBLICATIONS

European Patent Office, International Search Report for International Application No. PCT/EP2017/052336, dated Apr. 3, 2017.

* cited by examiner

VASCULAR PROSTHESIS WITH SIDE BRANCHES

CROSSREFERENCES TO RELATED APPLICATIONS

This application is a continuation of international patent application PCT/EP2017/052336, filed on Feb. 3, 2017, designating the U.S., which international patent application has been published in German language and claims priority from German patent application DE 10 2016 102 008.7, filed on Feb. 4, 2016. The entire contents of these priority applications are incorporated herein by reference.

BACKGROUND OF THE INVENTION

The present invention relates to a branched vascular prosthesis for a blood vessel of a patient.

It is generally known for intraluminal vascular prostheses or implants, also referred to as endovascular stents or stent grafts, to be used for treating weakened, damaged or torn vessels or aneurysms. For this purpose, a vascular implant or a stent graft is released at the diseased or damaged site of the vessel and restores the functionality of the original vessel or supports the still existing integrity of the vessel.

An aneurysm is understood here as a widening or bulging of an arterial blood vessel as a consequence of congenital or acquired lesions of the wall. The bulge in this case can affect the vessel wall as a whole or, in what is called a false aneurysm or dissection, blood flows from the lumen of the vessel in between the layers of the vessel wall and tears these apart from one another. Non-treatment of an aneurysm may lead in the advanced stage to a rupture of the artery, after which the patient suffers internal bleeding. The cause of a thoracic and thoracicoabdominal aortic aneurysm may be arterial sclerosis, high blood pressure and inflammation processes of the vessel wall. Injuries of the thorax due to serious accidents may also lead to acute or chronic aortic aneurysms.

The self-expanding vascular prostheses used for the treatment of aneurysms generally consist of a hollow-cylindrical metal framework of which the lateral surface is covered by a textile or polymer film, such that a hollow-cylindrical body is obtained. For implantation, the vascular implant is radially compressed, such that its cross-sectional area is greatly reduced. With the aid of an insertion system, the vascular implant is then brought into the area of the aneurysm, where it is released. By virtue of the resilience of the metal framework, the vascular implant expands again to its original shape and in so doing stretches its lateral surface, which lodges inside the blood vessel proximally and distally in relation to the aneurysm. In this way, the blood now flows through the vascular implant, and further loading of the bulge is prevented.

The metal framework of such vascular implants generally consists for example of a wire mesh or of so-called stent springs, which are arranged one behind the other, running around in a meandering formation, and if appropriate are connected to one another by connecting struts made of wire, or which are merely connected to one another via the material of the implant. The wire mesh or the stent springs are usually made of a shape-memory material, generally of Nitinol, as a result of which, after insertion into a vessel for release, the stent springs return to the expanded state and thus "open up" the vascular implant.

Aneurysms often occur in the area of the abdominal aorta (*Aorta abdominalis*) or thoracic aorta (*Aorta thoracica*), it being possible for a thoracic aneurysm to occur in what is called the ascending branch of the aorta (*Aorta ascendens*), in the aortic arch and/or in the descending branch of the aorta.

In the case of thoracicoabdominal aortic aneurysms, the aneurysm does not just remain confined to a limited part of the principal artery but is located both in the chest cavity, that is to say the thorax, and in the abdominal cavity (abdomen).

Thoracicoabdominal aorta aneurysm is a very complex disease and difficult to treat. Before the aortic stent became established, it was almost always necessary to open both the thorax and the abdominal cavity. Today it is alternatively possible in the course of hybrid operations for opening of the abdominal cavity to be performed in combination with an aortic stent, or for a total endovascular treatment of thoracicoabdominal aortic aneurysms to be performed.

In the case of thoracicoabdominal aortic aneurysms, the situation is almost always made more difficult by the fact that arteries of all the major organs (arteries of the intestines, *Truncus coeliacus*, arteries of the kidneys) are affected during the reparation and have to be reconstructed in some form or other. The therapy for a thoracicoabdominal aneurysm is therefore difficult, involves complications and is often carried out by special centers.

The vascular prostheses used in the therapy must meet many requirements, in particular with regard to the size, length and morphology of the aneurysm and native aorta to be bridged; the permeability of the segmental arteries in this area, the coexistence of other aneurysms and the diameter of the iliac and femoral vessels also play a great role.

As before, there is therefore still a great need for stent/stent graft systems, or vascular prostheses, with the aid of which the intervention described above could be made easier and reduced in time.

SUMMARY OF THE INVENTION

The object of the present invention is therefore to provide a system with which thoracicoabdominal aneurysms can be treated quickly and uncomplicatedly.

This object is achieved according to the invention by a preferably self-expanding vascular prosthesis comprising a hollow-cylindrical main body with a longitudinal axis, a proximal opening and a distal opening, and also a main lumen extending between the proximal opening and the distal opening, the main body having a proximal end portion and a distal end portion, which respectively comprise the first opening or the second opening, and also a middle portion arranged between the proximal end portion and the distal end portion; also comprising a multiplicity of stent rings, which are not connected to one another, are arranged running around in a meandering formation in the longitudinal direction of the vascular prosthesis and spaced apart one behind the other, the stent rings respectively having ogives and webs connecting them; also comprising a prosthesis material, to which the stent rings are attached, and also comprising at least four side branches, which extend, towards the distal direction, into and within the main lumen from fenestrations in the prosthesis material lying between the stent rings, each side branch having a first side-branch opening and a second side-branch opening and also a side-branch lumen extending between the first side-branch opening and the second side-branch opening, the first side-branch opening respectively being firmly attached to the prosthesis material by way in each case of a fenestration for the formation of a side-branch attachment; the vascular prosthesis according to the invention also has four side branches, which extend into the interior of the main lumen, and are arranged in the middle portion, the middle portion having a smaller diameter in comparison with the diameter of the end portions.

The object on which the invention is based is completely achieved in this way.

The self-expanding vascular prosthesis according to the invention provides a vascular prosthesis system with which thoracicoabdominal aneurysms can be successfully bridged, while at the same time reliably ensuring the supply of blood to the branching-off side vessels, that is to say for example the visceral arteries. This is achieved in the case of the vascular prosthesis according to the invention by the side branches/arms by way of which the side vessels are reliably supplied, in particular by connecting further connection stents/stent grafts, being routed in the interior of the main lumen of the vascular prosthesis. It is ensured by the inwardly routed branch-off of the side branches/arms that there is sufficient space for the vascular prosthesis in the vessel in which the vascular prosthesis is released, but at the same time the function of the arms/side branches is ensured. By contrast with proper fenestrations, branched vascular prostheses such as those concerned here have the advantage of a longer overlapping zone with connection stents/stent grafts for the branching-off side vessels.

The vascular prosthesis according to the invention also has the advantage that, as a result of the specific arrangement of the side branches branching off inwardly into the main lumen, what is known as an "off-the-shelf" system is provided, consequently therefore a vascular prosthesis that does not have to be individually made up in each case for the patient specifically to be treated, but instead can be prefabricated, particularly for a large number of patients, on account of its specific arrangement and dimensions of the side branches.

All four side branches of the vascular prosthesis according to the invention are arranged in the middle portion, which has a smaller diameter than the two portions arranged to the right and left, or proximally and distally, with respect to the middle portion.

The vascular prosthesis according to the invention itself, or the main body, is in this case formed in one piece, i.e. the stent rings, possibly of different diameters, are attached to, for example sewn onto, the prosthesis material at spacings in relation to one another. The stent rings may be sewn on the prosthesis material on the outside or inside.

The side branches preferably comprise a, or at least one, stent ring, which is attached to a prosthesis material—from the inside or from the outside.

It goes without saying that the side branches, which in the present case and in the prior art are also referred to as "arms" or "sleeves", in this case do not extend over the entire length of the vascular prosthesis, but only represent short stent graft portions, with which a connecting piece for stents/stent grafts that branch off into the side vessels and are to be connected is provided.

In principle, in the case of vascular prostheses or endoluminal stent grafts, the respective ends are generally, and in the present case, referred to by the terms "distal" and "proximal", where the term "distal" designates that part or end lying farther downstream in relation to the blood flow. By contrast, the term "proximal" designates, again in relation to the blood flow, a part or the end lying farther upstream in relation to the blood flow. To put it another way, the term "distal" means in the direction of the blood flow, and the term "proximal" means counter to the direction of the blood flow. In the case of catheters, by contrast, or insertion systems, the term "distal" designates the end of the catheter or insertion system that is inserted into the patient, or the end farthest away from the user, and the term "proximal" designates the end nearer the user.

According to the invention, the division of the main body of the vascular prosthesis into a proximal end portion, a middle portion and a distal end portion means that the respective portions differ from one another by a different type of construction, and for example have a different number of stent rings, or the stent rings thereof have different diameters, so that a different outer form of the portions with different diameters of the main body in these portions is obtained therefrom.

"Fenestration" means in the present case, and generally in the prior art, that the prosthesis material defining a lateral surface has in its lateral surface a, or at least one, opening, as it were a hole, whereby access to the main lumen, that is to say the interior of the main lumen, is provided. According to the invention, these fenestrations are prolonged inwardly, that is to say into the main lumen, through the side branches.

In a preferred embodiment of the vascular prosthesis according to the invention, all of the stent rings have the same diameter in the middle region.

In another preferred embodiment, both the proximal end portion and the distal end portion additionally have in each case a portion tapering in diameter to the middle portion.

According to an embodiment of the vascular prosthesis according to the invention, the webs of the stent rings that connect the ogives are shorter in the middle region than the webs that connect the ogives of the stent rings in the two end portions.

This embodiment has the advantage that, as a result, the stent rings in the middle region have a narrower diameter, to be precise as a result of the shorter formation of the webs. In other words, as a result, the stent rings in the middle portion have a smaller diameter than the stent rings in the distal or proximal portion, while the number of ogives remains the same.

In a further embodiment, the webs of all the stent rings in the middle region are of the same length. This means that the stent rings in the middle region all have the same, or substantially the same, diameter, and differ in their diameter from the stent rings of the proximal portion and the distal portion.

Preferably, an embodiment of the vascular prosthesis has in the middle portion four, five or six stent rings, the proximal portion three, four or five stent rings, and the distal portion two, three or four stent rings.

The stent rings of the vascular prosthesis according to the invention, running around in a meandering formation, are preferably produced from a self-expanding material with a shape-memory characteristic, and are preferably made of Nitinol. The stent rings have ogives alternately pointing in the proximal direction and the distal direction and webs connecting them. The side branches may also be constructed in this way. A more detailed description of such stents and of the material of the graft/prosthesis can be found for example in DE 103 37 739, to the entire content of which reference is hereby specifically made. The stent rings are secured to prosthesis material, it being preferred if the prosthesis material comprises a material that is selected from a textile or a polymer.

In particular, it is preferred if the prosthesis material comprises a material or is formed from a material that is selected from polyester, polyurethane, polystyrene, polytetrafluoroethylene, ultra-high-molecular-weight polyethylene (UHMPE), or mixtures thereof.

In a development of the vascular prosthesis according to the invention, the first side-branch opening of each side branch, which in each case is firmly attached to the prosthesis material by way in each case of a fenestration, has a substantially oval basic form.

"Substantially" means here that the opening does not have to be exactly oval, but that the form of the opening is of such a form that is still regarded as oval. This embodiment has the advantage that the branch-off of the side branches into the interior of the main lumen of the main body can be greatly angled, to be precise, according to one embodiment, virtually parallel to the longitudinal axis of the vessel prosthesis.

According to a further embodiment of the vessel prosthesis according to the invention, the second side opening of each side branch has a substantially circular basic form.

This embodiment achieves the effect that the free, second side-branch opening offers a uniform opening, into which for example connection stent grafts/stents can be easily introduced.

According to a development of the vascular prosthesis according to the invention, the side branches in the middle portion are arranged in such a way that the side-branch attachment of a first side branch is turned, with respect to the longitudinal axis of the main body, between 5 and 15°, preferably by 10°, in such a way that the side branch protrudes into the main lumen at an angle of 10° with respect to the longitudinal axis, and that the side-branch attachments of the three other side branches are unturned with respect to the longitudinal axis. In this case, "unturned" means that the unturned side branches run substantially parallel to the longitudinal axis, whereas "turned" means that the correspondingly turned side branch, or the turned side-branch opening, extends at an angle from the longitudinal axis. Since the first side-branch opening in a preferred embodiment has an oval basic form, it goes without saying that the unturned arrangement of the side-branch attachment means that the longer diameter of the oval basic form is parallel to the longitudinal axis.

The turning of a side-branch opening in relation to the longitudinal axis L achieves the effect that it protrudes at an angle from the longitudinal axis of the vascular prosthesis; this in turn achieves the effect that the side-branch opening of the turned side branch does not collide with the other side branches, or the one arranged closest. The handling and influencing of the side branches is thereby made significantly easier.

According to a development of the vascular prosthesis according to the invention, in the middle portion two side branches are arranged more distally than the two other, proximal, side branches. Correspondingly, the vascular prosthesis according to the invention comprises two most proximally arranged side branches and two most distally arranged side branches.

Altogether, it is preferred in the case of the vascular prosthesis according to the invention if the side branches or the first side branch opening attachments thereof are respectively arranged between two stent rings.

It is preferred in this case if all the side branches are arranged distributed and offset over the middle portion, to be precise in such a way that the side-branch attachment of the two most distally arranged side branches, which both lie distally in relation to the other two most proximally arranged side branches, are arranged between the same stent rings. It is also preferred if the side-branch attachment of the most proximally arranged side branch and of the side branch arranged downstream thereof in the distal direction are arranged between two different stent rings.

According to a further embodiment of the vascular prosthesis according to the invention, the side-branch attachments of the most proximal side branches are arranged offset in relation to one another in the circumferential direction of the hollow-cylindrical main body.

This embodiment has the advantage that the side branches or the free second side-branch opening thereof do not overlap and do not collide with one another.

In a development, it is preferred if the side-branch attachments of the two most proximal side branches are arranged offset in relation to one another in the circumferential direction with respect to the side-branch attachments of the two most distally arranged side branches.

This embodiment has the advantage that all four side branches do not overlap in the main lumen, consequently also do not collide, so that their handling is significantly improved.

According to a preferred embodiment of the vascular prosthesis according to the invention, the side-branch attachment of the most proximally arranged side branch and the side-branch attachment of the side branch arranged downstream thereto in the distal direction are arranged offset in relation to one another at a circumferential angle of about 25° to 35°, preferably of about 29° to 32°.

According to a further embodiment of the vascular prosthesis according to the invention, the side-branch attachment of the two most distally arranged side branches are arranged offset in relation to one another at a circumferential angle of about 140° to 160°, preferably of about 149° to about 152°.

"Circumferential angle" means here in the present case that the side-branch attachments are arranged distributed at a certain angle in relation to one another over the circumference of the hollow-cylindrical main body.

In a further embodiment of the vascular prosthesis according to the invention, the side-branch attachment of the most proximally arranged side branch and the side-branch attachment of the side branch arranged downstream thereof in the distal direction are spaced apart from one another, with respect to a respective midpoint of the side-branch attachments, in the longitudinal direction by between about 15 and 25 mm, preferably between about 18 and 22 mm.

The term "about" means here in the present case that the values specified do not always have to be realized exactly, i.e. to zero after the decimal point, but that slightly diverging values of for example 14.95 to 15.05 mm are also included.

In a development of the vascular prosthesis according to the invention, the side-branch attachment of the second most proximally arranged side branch and the side-branch attachment of the side branch arranged downstream thereof in the distal direction are spaced apart from one another, with respect to a respective midpoint of the side-branch attachments, in the longitudinal direction by between about 12 and 20 mm, preferably between about 14 and 18 mm.

It is also preferred according to a further embodiment if the side-branch attachment of the third most proximally arranged side branch and the side-branch attachment of the side branch arranged downstream thereof in the distal direction are spaced apart from one another, with respect to a respective midpoint of the side-branch attachments, in the longitudinal direction by between about 2 and 6 mm, preferably between about 3.5 and 4.5 mm.

In the course of the development of the present invention, it was discovered that, with the preferred values specified above for the circumferential angles and also the spacing of the side-branch attachments from one another, it was possible to provide a vascular prosthesis that is suitable as an off-the-shelf product in particular for the aorta in the area of the origins of the *Truncus coeliacus*, of the *Arteria mesenterica* superior, and also of the right and left renal arteries (*Arteria renalis dextra* and *Arteria renalis sinistra*). In this case, the most proximally arranged side branch is assigned to the *Truncus coeliacus*, the side branch following it in the distal direction is assigned to the *Arteria mesenterica* superior, and the two most distally arranged side branches are assigned to the right and left renal arteries, respectively.

In a development of the vascular prosthesis according to the invention, the proximal end portion has a greater diameter than the distal end portion, it being preferred according to a development if the proximal end portion has a tapering portion at the transition to the middle portion. Furthermore, the distal end portion may have a portion tapering toward the middle portion at the transition to the middle portion.

According to a preferred embodiment, the proximal end portion has a length of between about 58 and 70 mm, preferably of between about 62 and 66 mm, the tapering portion of the proximal portion has a length of about 20 to 32 mm, preferably about 24 to 28 mm, the middle portion has a length of about 56 to 68 mm, preferably about 60 to 64 mm, the distal portion tapering toward the middle portion has a length of about 13 to 25 mm, preferably of about 17 to 21 mm, and the distal end portion has a length of about 28 to 40 mm, preferably of about 32 to about 36 mm. The overall length of the proximal end portion is in this case about 86 to about 96 mm, preferably about 88 to 92 mm; the overall length of the distal end portion is about 40 to 52 mm, preferably 44 to 48 mm.

The overall length of the vascular prosthesis is preferably between about 190 and 220 mm, preferably between about 200 and 210 mm, and is still more preferably about 205 mm.

In a further embodiment, it is preferred if the diameter of the side-branch lumen with the first and second proximal side-branch attachments is of between about 7 and 9 mm, and is preferably 8 mm.

According to a further embodiment of the vascular prosthesis according to the invention, it is preferred if the diameter of the side-branch lumen with the first and second distal side-branch attachments is in each case between about 5 and 7 mm, and is preferably 6 mm.

It is in this case also preferred, in a further embodiment, if the greatest diameter of the substantially oval basic form of the first side-branch openings is of between about 12 to 18 mm, and is preferably about 15 mm.

In a development of the vascular prosthesis according to the invention, radiopaque markers are provided at least in the region of its ends and/or the side-branch ends and/or in the region of the branch-off/the openings of the inwardly branching-off side branches.

Preferably, the radiopaque markers are made of one or more of the following materials, for example gold, palladium, tantalum, chromium, silver, etc.; the form of the markers may in this case be any desired form, for example round, angular, and/or for example have the form of letters, numbers or figures that are helpful for the orientation of the prosthesis in the vessel.

In an embodiment of the vascular prosthesis according to the invention, the stent ring attached at the proximal end of the vascular prosthesis is only fastened to the prosthesis material by way of its distally facing ogives, but not its proximally facing ogives.

According to the further embodiment, the proximal and distal portions may have stent rings with different ogives, i.e. extending with different amplitudes in the distal and proximal directions. In a preferred development, the side branches may also have at least one, preferably one, stent ring with different amplitudes of the ogives.

Further advantages will become clear from the figures and from the following description of preferred exemplary embodiments.

It will be appreciated that the aforementioned features and the features still to be explained below can be used not only in the respectively specified combination but also in other combinations or on their own without departing from the scope of the present invention.

BRIEF DESCRIPTION OF THE DRAWINGS

Exemplary embodiments of the invention are explained in more detail in the description below and are shown in the drawing, in which:

FIG. 1 shows a schematic representation of an embodiment of a vascular prosthesis according to the invention in the non-inserted, expanded state in a perspective view of the longitudinal side from laterally-above;

FIGS. 2 A-B show the embodiment from FIG. 1 in a completely lateral view of the longitudinal side, with schematic depiction of the stent rings and side branches; from one side (FIG. 2A), and in a view of a further side (FIG. 2B);

FIGS. 3 A-B show the representation of an isolated side branch, in a view of the first side-branch opening from above (FIG. 3A), and from the side (FIG. 3B);

FIGS. 4 A-C shows a further schematic representation of an embodiment of a vascular prosthesis according to the invention, the stent rings not being depicted here for the sake of a better overview; in a view from one side (FIG. 4A), another side (FIG. 4B), and also in a view looking into the main lumen (FIG. 4C).

DESCRIPTION OF PREFERRED EMBODIMENTS

In the figures, identical features are provided with identical reference signs, not all of the figures always showing all of the reference signs for reasons of overall clarity.

Figures 1, 2A:
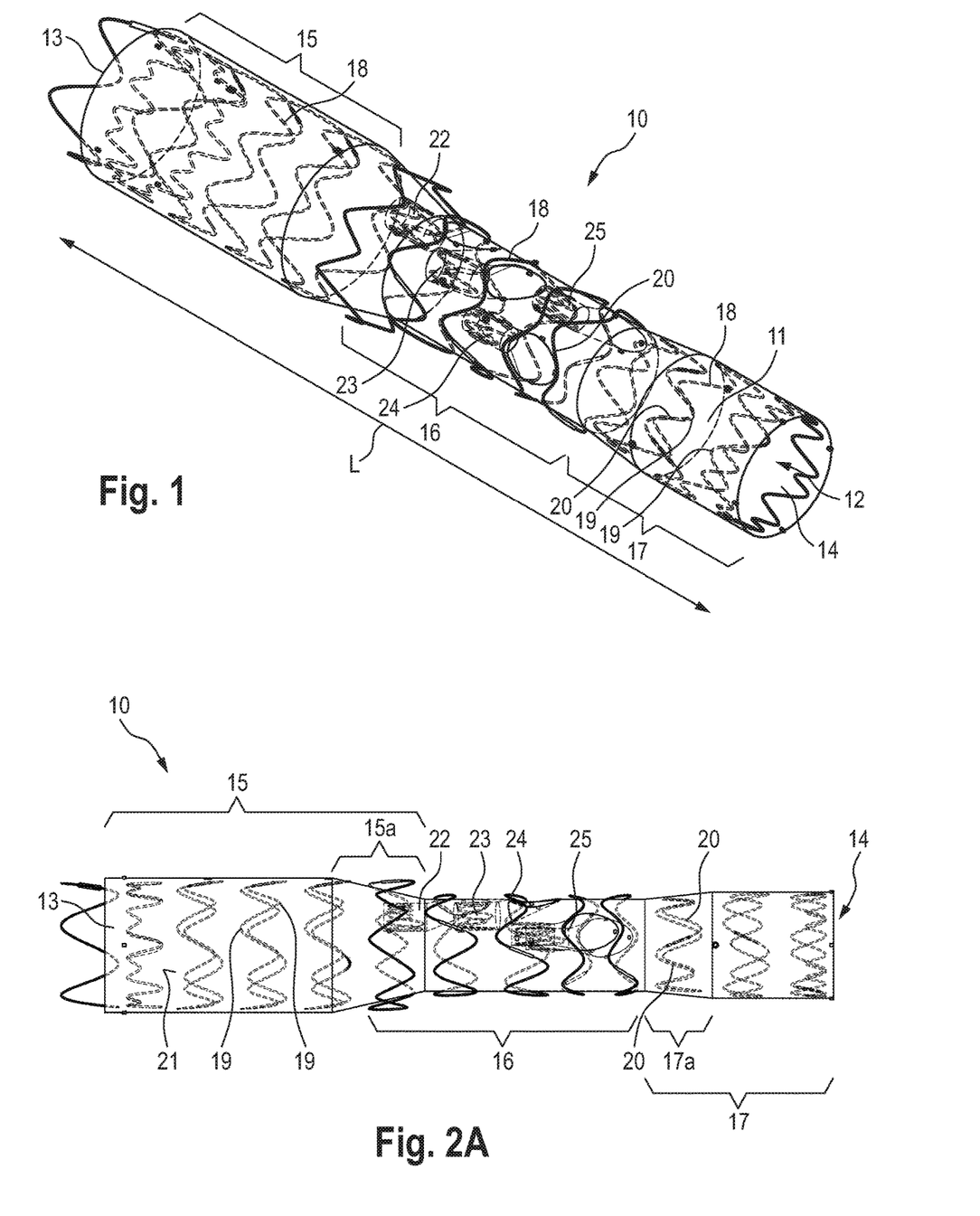
Figure 2B:
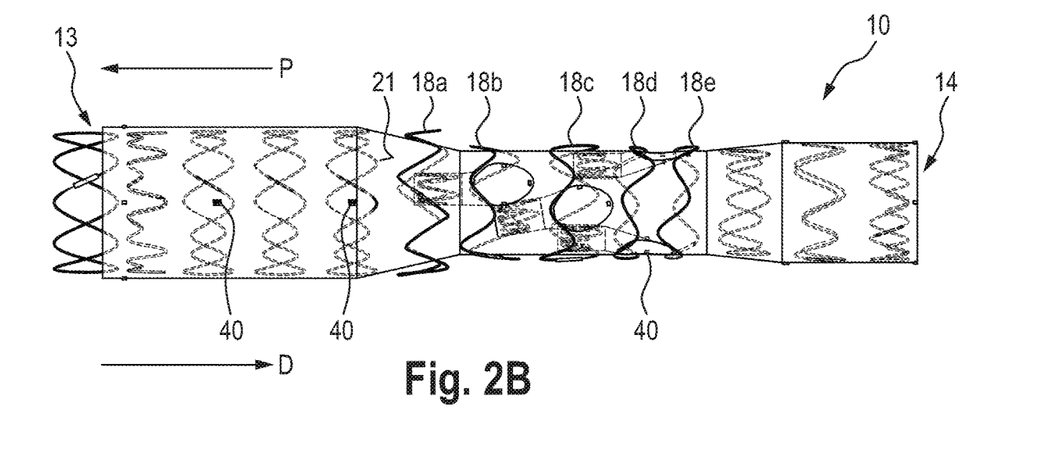

In FIGS. 1, 2 A-B, 3 A-B, and 4 A-C, reference sign 10 designates the whole of a vascular prosthesis, comprising a generally hollow-cylindrical main body 11 with a longitudinal axis L, a proximal opening 13 and a distal opening 14. The vascular prosthesis 10 also has a main lumen 12 extending between the proximal opening 13 and the distal opening 14. The main body 11 comprises a proximal end portion 15 and a distal end portion 17, and also a middle portion 16 arranged therebetween. The proximal end portion 15 in this case comprises the proximal opening 13; the distal end portion 17 comprises the distal opening 14.

As can be seen from FIG. 1 and FIGS. 2 A-B, the vascular prosthesis 10 comprises a multiplicity of individual stent rings 18 that are not connected to one another. These stent rings 18 are formed in one piece, i.e. in a closed annular manner, and running around in a meandering formation. The stent rings 18 are also arranged one behind the other over the longitudinal axis L of the vascular prosthesis 10 at a spacing from one another in such a way that they do not touch one another. The stent rings 18 are formed by ogives 19 facing alternately in the proximal direction and the distal direction and webs 20 connecting them.

The stent rings 18 are attached to a prosthesis material 21, and thereby indirectly connected to one another.

In FIG. 2B, the distal direction is indicated by the arrow "D", and the proximal direction by the arrow "P".

The middle portion 16 also has a diameter d2, which is smaller than the diameters d1 and d3 of the end portions 15 and 17.

As can be seen in particular from FIGS. 2A and 2B, the proximal end portion 15 comprises a portion 15a tapering toward the middle portion 16, and the distal end portion 17 comprises a portion 17a tapering toward the middle portion 16. In the example shown in FIGS. 1 and 2 A-B, the tapering of these portions is brought about by stent rings 18 with a smaller diameter than the stent rings 18 of the respective end portions 15, 17. The diameter of the proximal end portion 15 is in this case greater than the diameter of the distal end portion 17, the middle portion 16 having the smallest diameter. The diameters of the tapering portions 15a, 17a of the proximal portion 15 and of the distal portion 17 in this case taper continuously toward the middle portion.

It can also be seen from the figures that the middle portion 16 comprises four side branches 22, 23, 24, 25, which branch off inwardly, that is to say into the main lumen 12. The four side branches 22, 23, 24 and 25 extend from fenestrations 26 present in the prosthesis material in the direction distally into the main lumen 12 and in the main lumen 12 (see FIGS. 4A, 4B).

The side branches 22, 23, 24 and 25 respectively comprise a first side-branch opening 27 and a second side-branch opening 28 (see FIGS. 4A and 3B), and also a side-branch lumen 29 extending between these openings 27, 28. The first opening 27 is in this case firmly attached to the prosthesis material 21 of the main body 11, to be precise by way of the fenestration 26, for the formation of a side-branch attachment 30. The second opening 28 is free in the main lumen 12.

Figure 3A:
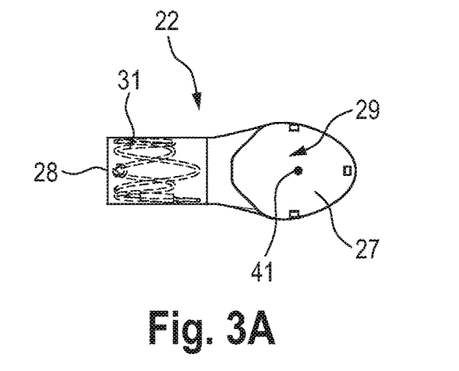
Figure 3B:
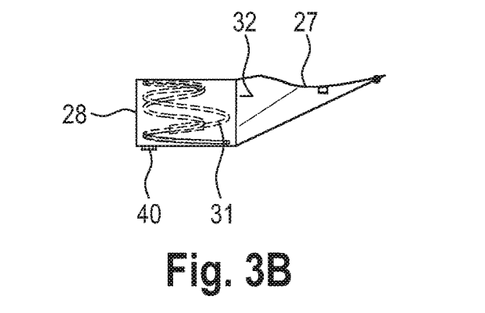

The side branches 22, 23, 24 and 25 respectively have a stent ring 31, which is provided in the region of the second opening 28, whereby this opening is kept open. The stent ring 31 forms together with a prosthesis material 32 (see FIGS. 3 A-B) the side branch 22, 23, 24, and 25.

As can be seen in particular from FIGS. 3A and 3B, in which the side branch 22 is shown in detail, and which is identical in construction to the side branches 23, 24, and 25, the first side-branch opening 27 has a substantially oval basic form, whereas the second side-branch opening 28 has a substantially round opening, brought about by the annular stent ring 31.

Figure 4A:
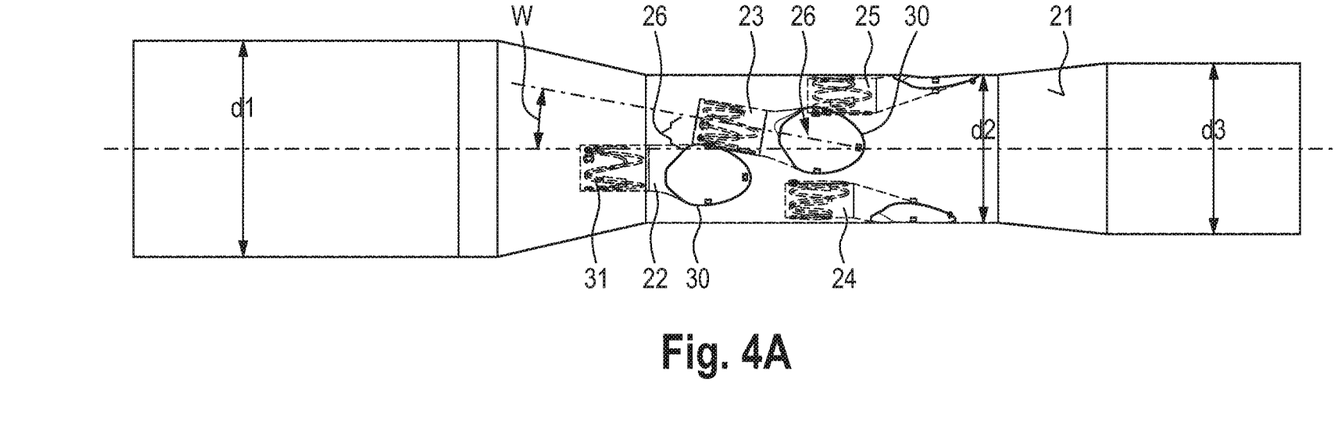
Figure 4B:
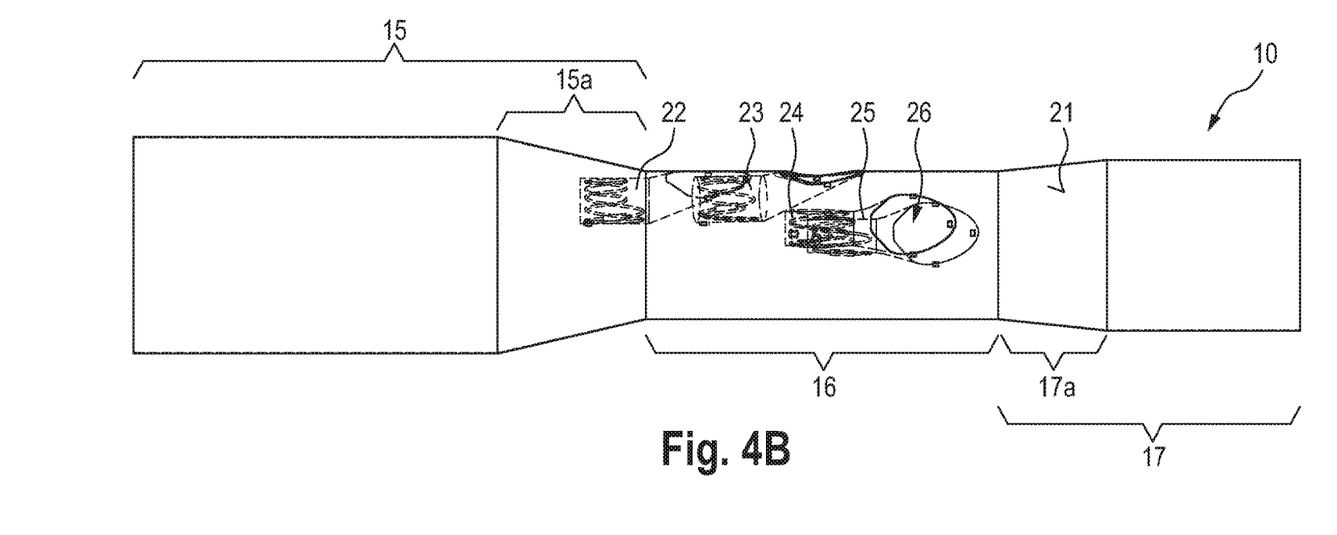

It can also be seen from the figures that the four side branches 22, 23, 24 and 25 are arranged in such a way that the two side branches 22 and 23 are located proximally in relation to the side branches 24 and 25, the side branch 22 being arranged the most proximally, and the side branch 25 being arranged the most distally. It can be seen here from FIG. 4A that the proximal side branch 23, or the side-branch attachment 30 thereof that is arranged downstream of the most proximal side branch 23 in the distal direction, is attached such that it is turned with respect to the longitudinal axis L of the vessel prosthesis 10, which is indicated in FIG. 4A by the angle W. The other side-branch attachments 30 of the side branches 22, 24 and 25 are attached parallel to the longitudinal axis L of the vessel prosthesis. It can be seen here in the figures that a "turning" means that the oval basic form of the side-branch opening 29, which in the unturned arrangement is arranged with its longer diameter parallel to the longitudinal axis L of the vessel prosthesis, is turned with respect to its longer diameter and with respect to the longitudinal axis L of the vessel prosthesis at a certain angle, preferably 8°, 9°, 10°, 11° or 12°.

As can also be seen from FIGS. 1 and 2 A-B, the side-branch attachments 30 of the proximal side branches 22 and 23 in the middle portion 16 are not arranged between the same stent rings 18, whereas the side-branch portions 30 of the distal side branches 24 and 25 are arranged between the same stent rings 18, the latter being offset somewhat with respect to the circumferential angle of the vascular prosthesis 10.

In the example shown in FIGS. 1 and 2 A-B, the middle portion 16 has five stent rings 18a to e, which are arranged one behind the other from proximal to distal. The side-branch attachment 30 of the most proximal side branch 22 is in this case arranged between the stent rings 18b and 18c, the side-branch attachment 30 of the side branch 23 is arranged between the stent rings 18c and 18d, and the two side-branch attachments 30 of the side branches 24, 25 are arranged between the stent rings 18d and 18e.

The side-branch attachments 30 of the side branches 22, 23, 24, 25 are arranged offset in relation to one another over the circumference or the lateral surface of the middle portion 16 of the vascular prosthesis 10, so that in an identical imaginary line along the longitudinal axis L of the vascular prosthesis there is no side branch 22, 23, 24, 25.

Figure 4C:
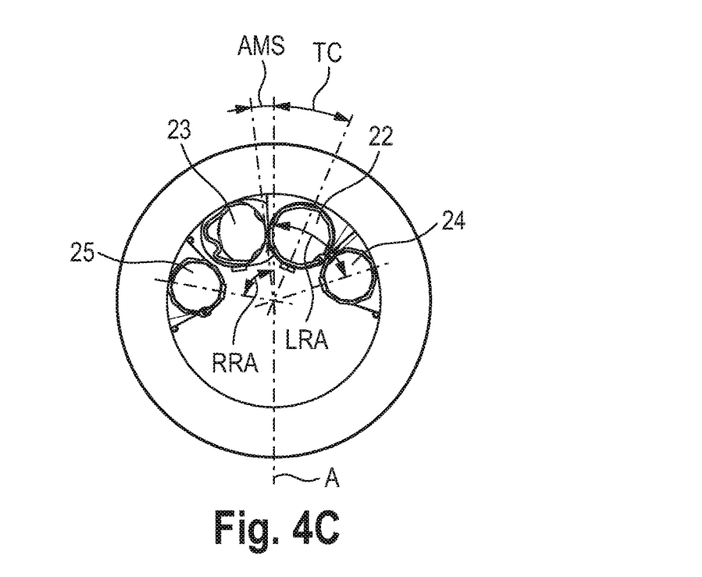

This offset arrangement of the side-branch attachments 30 of the side branches 22, 23, 24, 25, differing in the circumferential angle, is shown in particular in FIG. 4C: here, a perpendicular axis through the cross section of the vascular prosthesis is shown by the line A, to be precise from the proximal direction looking into the vascular prosthesis 10. Here it can be seen that the side branch 22 or the side-branch attachment 30 thereof is displaced at an angle TC, preferably by 10°, and that the side branch 23, or the side-branch attachment 30 thereof, is turned by an angle AMS, preferably 8°, so that the side branches 22, 23, 24, 25 are completely open, and do not cover one another, and thereby make the opening smaller. It is indicated by the circumferential angles RRA and LRA how the two distal side-branch attachments 30 of the side branches 24, 25 are arranged angularly in relation to the attachment 30 of the side branch 23.

Also provided in the example shown in FIGS. 1, 2 A-B and 3 A-B are X-ray markers, which are indicated in FIGS. 2 A-B by the arrows 40. As can be seen in particular from FIG. 2B, markers 40 are provided along the longitudinal axis L of the vascular prosthesis, and also in the region of the side-branch attachments 30 of the side branches 22, 23, 24, 25. There are also markers 40 in the region of the second opening of the side branches 22, 23, 24, and 25, as can be seen from FIGS. 3 A-B.

In the example shown in FIGS. 1, 2 A-B, and 3 A-B, the length of the vascular prosthesis is about 205 mm.

In the example shown in FIGS. 1, 2 A-B and 3 A-B, the circumferential spacing of the attachments 30 of the side branches 22, 23, 24, and 25 is as follows: the attachment 30 of the most proximal side branch 22 is spaced apart—with respect to a midpoint 41 of the attachments—from the attachment 30 of the side branch 23, which lies distally from the attachment 30 of the side branch 22, by preferably 20 mm of the side branch 22; furthermore, the attachment 30 of the side branch 23 is preferably spaced apart from the attachment 30 of the side branch 24, which lies proxiamally with respect to the attachment 30 of the distal side branch 25, by 16 mm; and the attachment 30 of the side branch 24 is preferably spaced apart from the attachment 30 of the distal side branch 25 by 4 mm. In this case, the spacing thereby specified means the spacing measured over the longitudinal axis, the attachments 30 of the side branches 22, 23, 24 and 25, as mentioned above, being offset circumferentially.

The vascular prosthesis 10 according to the invention is advantageously used for the treatment of a thoracicoabdominal aortic aneurysm of a human patient, in particular in the area of the origins of the *Truncus coeliacus*, of the *Arteria mesenterica* superior, and also of the right and left renal arteries. In this case, the side branch 22 is intended or designed for the *Truncus coeliacus*, the side branch 23 is intended or designed for the *Arteria mesenterica* superior, and the two distal side branches 24, 25 are intended or designed for the *Arteria renalis dextra* and *Arteria renalis sinistra*, respectively.

What is claimed is:

1. A vascular prosthesis for a blood vessel of a patient, which has the following:
    a hollow-cylindrical main body with a longitudinal axis (L), a proximal opening and a distal opening, and also a main lumen extending between the proximal opening and the distal opening, wherein a direction of blood flow is from proximal to distal, the main body having a proximal end portion and a distal end portion, which respectively comprise the proximal opening or the distal opening, and also a middle portion arranged between the proximal end portion and the distal end portion, the proximal end portion, the middle portion, and the distal end portion each having diameters d1, d2, and d3, respectively, wherein both the proximal end portion and the distal end portion have in each case a portion tapering in diameter towards the middle portion,
    a plurality of stent rings, which are not directly connected to one another, the stent rings being arranged spaced apart one behind the other in the longitudinal direction of the vascular prosthesis and running around in a meandering formation, the stent rings respectively having ogives and webs connecting the ogives,
    a prosthesis material, to which the stent rings are attached, and
    four side branches, which extend, from fenestrations in the prosthesis material lying between the stent rings, exclusively into and within the main lumen towards the distal proximal opening, such that no parts of the side branches extend outside the lumen, each side branch having a first side-branch opening and a second side-branch opening and also a side-branch lumen extending between the first side-branch opening and the second side-branch opening, the first side-branch opening respectively being firmly attached to the prosthesis material by way of a fenestration for the formation of a side-branch attachment, wherein the four side branches are arranged in the middle portion, wherein the middle portion has a smaller diameter d2 in comparison with the diameters d1 and d3 of the proximal end portion and distal end portion, respectively.

2. The vascular prosthesis as claimed in claim 1, wherein the stent rings in the middle region have the same diameter.

3. The vascular prosthesis as claimed in claim 1, wherein the first side-branch opening of each side branch, which is firmly attached to the prosthesis material by way of a fenestration, has an oval basic form.

4. The vascular prosthesis as claimed in claim 1, wherein the second side-branch opening of each side branch has a circular basic form.

5. The vascular prosthesis as claimed in claim 1, wherein the side branches in the middle portion are arranged in such a way that the side-branch attachment of a first side branch is turned, with respect to the longitudinal axis L of the main body, between 5 and 15°, in such a way that the side branch protrudes into the main lumen at an angle of 10° with respect to the longitudinal axis L, and in that the side-branch attachments of the other three ether side branches are unturned with respect to the longitudinal axis L.

6. The vascular prosthesis as claimed in claim 1, wherein the side branches are distributed and offset over the middle portion in such a way that the side-branch attachment of a first side branch and the side-branch attachment of a second side branch, which first and second side branches are both distally arranged in relation to a third and fourth side branches, are arranged between the same stent rings, and the side-branch attachment of the most proximally arranged side branch and of the side branch arranged consecutively downstream thereof in the distal direction are arranged between two different stent rings.

7. The vascular prosthesis as claimed in claim 6, wherein the side-branch attachments of the most proximal side branches are arranged offset in relation to one another in the circumferential direction of the hollow-cylindrical main body.

8. The vascular prosthesis as claimed in claim 6, wherein the side-branch attachments of the two most proximal side branches are arranged offset in relation to one another in the circumferential direction with respect to the side-branch attachments of the two most distal side branches.

9. The vascular prosthesis as claimed in claim 6, wherein the side-branch attachment of a most proximal side branch and the side-branch attachment of a side branch arranged thereto in the distal direction are arranged offset in relation to one another at a circumferential angle of about 25° to 35°.

10. The vascular prosthesis as claimed in claim 6, wherein the side-branch attachment of two most distal side branches are arranged offset in relation to one another at a circumferential angle of about 140° to 160°.

11. The vascular prosthesis as claimed in claim 6, wherein the side-branch attachment of a most proximal side branch and the side-branch attachment of a side branch downstream thereof in the distal direction are spaced apart from one another, with respect to a respective midpoint of the side-branch attachments, in the longitudinal direction by between about 15 and 25 mm.

12. The vascular prosthesis as claimed in claim 6, wherein the side-branch attachment of a first side branch and the side-branch attachment of a second side branch arranged downstream thereof in the distal direction are spaced apart from one another, with respect to a respective midpoint of the side-branch attachments, in the longitudinal direction by between about 12 and 20 mm.

13. The vascular prosthesis as claimed in claim 6, wherein the side branch attachment of a first side branch and the side-branch attachment of a second side branch arranged downstream thereof in the distal direction are spaced apart from one another, with respect to a respective midpoint of the side-branch attachments, in the longitudinal direction by between about 2 and 6 mm.

14. The vascular prosthesis as claimed in claim 6, wherein the diameter of the side-branch lumen of two most proximally arranged side branches is of between about 7 and 9 mm.

15. The vascular prosthesis as claimed in claim 6, wherein the diameter of the side-branch lumen of two most distally arranged side branches is in each case between about 5 and 7 mm.

16. The vascular prosthesis as claimed in claim 3, wherein the greatest diameter of the oval basic form of the first side-branch openings is of between about 12 to 18 mm.

* * * * *